United States Patent [19]
Lam et al.

[11] Patent Number: 5,324,447
[45] Date of Patent: Jun. 28, 1994

[54] METHOD AND ACTIVATOR COMPOSITIONS TO DISINFECT LENSES

[75] Inventors: Sam W. Lam, Laguna Niguel; Paul S. Ripley, Irvine; J. Abraham M. Espiritu, Oceanside, all of Calif.

[73] Assignee: Allergan, Inc., Irvine, Calif.

[21] Appl. No.: 906,817

[22] Filed: Jun. 30, 1992

Related U.S. Application Data

[63] Continuation-in-part of Ser. No. 664,601, Mar. 4, 1991, which is a continuation-in-part of Ser. No. 416,074, Oct. 2, 1989, Pat. No. 5,078,908, Ser. No. 461,405, Jan. 5, 1990, Pat. No. 5,279,673, and Ser. No. 461,540, Jan. 5, 1990, Pat. No. 5,997,626.

[51] Int. Cl.$^5$ .............................. A61L 2/18; B08B 3/08
[52] U.S. Cl. ............................ 252/187.21; 252/187.23; 252/187.25; 252/187.26; 252/187.27; 424/661; 424/662; 435/264
[58] Field of Search ................ 424/665, 663, 661, 662; 252/187.21, 187.23, 187.24, 187.25, 187.26, 187.27, 187.28; 435/264

[56] References Cited

U.S. PATENT DOCUMENTS

| | | |
|---|---|---|
| Re. 23,218 | 4/1950 | Levy ........................ 162/87 |
| Re. 31,779 | 12/1984 | Alliger ...................... 252/187.23 |
| Re. 32,672 | 5/1988 | Huth et al. ................ 252/95 |
| 2,436,134 | 2/1948 | Aston ........................ 423/477 |
| 3,123,521 | 3/1964 | Wentworth ................ 424/615 |
| 3,278,447 | 10/1966 | McNicholas .............. 252/186.21 |
| 3,591,515 | 7/1971 | Lovely ...................... 252/186.22 |
| 3,819,828 | 6/1974 | McCoy ...................... 424/71 |
| 3,910,296 | 10/1975 | Karageozian et al. .... 134/2 |
| 3,912,451 | 10/1975 | Gaglia, Jr. ................ 422/30 |
| 4,011,941 | 3/1977 | Parsons .................... 206/5.1 |
| 4,084,747 | 3/1978 | Alliger ...................... 422/20 |
| 4,104,190 | 8/1978 | Hartshorn ................ 252/187.21 |
| 4,123,376 | 10/1978 | Gray ........................ 252/99 |
| 4,146,496 | 3/1979 | Gray ........................ 252/99 |
| 4,386,160 | 5/1983 | Banner-Jorgensen .... 435/221 |
| 4,456,510 | 6/1984 | Murakami ................ 204/101 |
| 4,459,217 | 7/1984 | Bogie ........................ 252/174.14 |
| 4,499,077 | 2/1985 | Stockel et al. ............ 424/661 |
| 4,557,925 | 12/1985 | Lindahl et al. ............ 424/482 |

(List continued on next page.)

FOREIGN PATENT DOCUMENTS

| | | |
|---|---|---|
| 520668 | 12/1987 | Australia . |
| 0082798 | 6/1983 | European Pat. Off. . |
| 0147100 | 7/1985 | European Pat. Off. . |
| 0168253 | 1/1986 | European Pat. Off. . |
| 0196075 | 1/1986 | European Pat. Off. . |
| 0199385 | 10/1986 | European Pat. Off. . |
| 0209071 | 1/1987 | European Pat. Off. . |
| 0240315 | 10/1987 | European Pat. Off. . |
| 0279401 | 2/1988 | European Pat. Off. . |
| 0255041A1 | 5/1988 | European Pat. Off. . |
| 0278224 | 8/1988 | European Pat. Off. . |
| 0384666 | 8/1990 | European Pat. Off. . |
| 0426489 | 5/1991 | European Pat. Off. . |
| 0458578A2 | 11/1991 | European Pat. Off. . |
| 3626082A1 | 11/1988 | Fed. Rep. of Germany . |

(List continued on next page.)

OTHER PUBLICATIONS

Chemical Abstracts Selects: Issue 2, 1987.
Eudragit L Data Sheet (Info L-2/e).
Siu et al, "Effect of Succinylation on the Protein Quality and Urinary Excretion of Bound and Free Amino Acids", J. Agric. Food Chem. 1982, 30, 1179-1183.
Communications to the Editor, "Stabilization of Microbial Proteases against Autolysis Using Acylation with Dicarboxylic Acid Anhydrides", Biotechnology and Bioengineering, vol. XXIV, pp. 483-486 (1982).

(List continued on next page.)

*Primary Examiner*—Robert L. Stoll
*Assistant Examiner*—Valerie Fee
*Attorney, Agent, or Firm*—Frank J. Uxa

[57] ABSTRACT

Methods for disinfecting a lens is disclosed. The methods comprise contacting a lens to be disinfected in a liquid medium with at least one chlorine dioxide precursor in the presence of at least one activator component selected from organic acid anhydrides, oxygen-releasing components and mixtures thereof to effect formation of chlorine dioxide from the chlorine dioxide precursor, thereby disinfecting the lens. Compositions useful in the above-noted methods are also disclosed.

15 Claims, No Drawings

U.S. PATENT DOCUMENTS

| | | | |
|---|---|---|---|
| 4,568,517 | 2/1986 | Kaspar et al. | 422/30 |
| 4,614,549 | 9/1986 | Ogunbiyi et al. | 134/19 |
| 4,618,444 | 10/1986 | Hudson et al. | 252/92 |
| 4,654,208 | 3/1987 | Stockel et al. | 424/78.08 |
| 4,689,215 | 8/1987 | Ratcliff | 424/53 |
| 4,690,773 | 9/1987 | Ogunbuyi et al. | 252/174.12 |
| 4,767,559 | 8/1988 | Kruse et al. | 252/106 |
| 4,792,442 | 12/1988 | Ratcliff | 408/54 |
| 4,855,135 | 8/1989 | Ratcliff | 424/661 |
| 4,861,514 | 8/1989 | Hutchings | 252/187.21 |
| 4,986,990 | 1/1991 | Davidson et al. | 424/665 |
| 4,997,626 | 3/1991 | Dziabo et al. | 422/37 |
| 5,077,258 | 12/1991 | Phillips | 502/321 |
| 5,078,908 | 1/1992 | Ripley et al. | 252/187.21 |
| 5,129,999 | 7/1992 | Holland et al. | 204/131 |
| 5,135,623 | 8/1992 | Dziabo et al. | 204/101 |
| 5,152,912 | 10/1992 | Dziabo et al. | 252/106 |

FOREIGN PATENT DOCUMENTS

| | | |
|---|---|---|
| WO8504107 | 9/1985 | PCT Int'l Appl. . |
| WO8605695 | 10/1986 | PCT Int'l Appl. . |
| WO8911878 | 12/1989 | PCT Int'l Appl. . |
| WO9006126 | 6/1990 | PCT Int'l Appl. . |
| WO9109630 | 7/1991 | PCT Int'l Appl. . |
| WO9109632 | 7/1991 | PCT Int'l Appl. . |
| WO9109690 | 7/1991 | PCT Int'l Appl. . |
| WO9215334 | 9/1992 | PCT Int'l Appl. . |
| 1269677 | 4/1982 | United Kingdom . |
| 2139260A | 11/1984 | United Kingdom . |
| 2173017A | 10/1986 | United Kingdom . |
| 2187748A | 9/1987 | United Kingdom . |
| 2187748 | 9/1987 | United Kingdom . |
| 2151039A | 7/1988 | United Kingdom . |

OTHER PUBLICATIONS

Kennedy et al., "The Oxidation of Organic Substances by Potassium Peroxymonosulfate", J. Organic Chemistry 25:1901–1906 (1960).

Polymers Letters Edition, "A Study of Ozone Attack on Elastomer Surfaces by Attenuated Total Reflectance Spectroscopy", vol. 12, pp. 281–286 (1974).

Manivannan et al, "Peroxo Salts As Initiators Of Vinyl Polymerization–III", Eur. Polym. J. vol. 23, No. 4, pp. 311–313 (1987).

Evans et al, "Phase Transfer Controlled Selective Oxidation Of Diarylsulfides to Diarylsulfoxides Using Potassium Hydrogen Persulfate", Synthetic Communications, 16(10), 1207–1216 (1986).

Bloch et al, "Epoxidation of Alkenes with Potassium Hydrogen Persulfate", J. Org. Chem. 1985, 50, 1544–1545.

Ball, Jr. et al., "Acylation of Egg White Proteins with Acetic Anhydride and Succinic Anhydride", Poultry Science 1982 61:1041–1046.

W. Masschelein, "Preparation of Pure Chlorine Dioxide", vol. 6, No. 2, Jun. 1967.

I. Klotz, "Succinylation", Methods in Enzymology, vol. XI, Enzyme Structure, 1967, 576–580.

De Poorter et al, "Oxone As Oxygen Donor In The Catalytic Hydroxylation Of Saturated Hydrocarbons", Tetrahedron Letters, vol. 26, No. 37, pp. 4459–4462 (1985).

Trost et al, "Chemoselective Oxidation of Sulfides to Sulfones with Potassium Hydrogen Persulfate", Tetrahedron Letters, vol. 22, No. 14, pp. 1287–1290 (1981).

METHOD AND ACTIVATOR COMPOSITIONS TO DISINFECT LENSES

RELATED APPLICATIONS

This application is a continuation-in-part of copending application Ser. No. 664,601, filed Mar. 4, 1991 which, in turn, is a continuation-in-part of each of the following applications: Ser. No. 416,074 filed Oct. 2, 1989 now U.S. Pat. No. 5,078,908; Ser. No. 461,405, now U.S. Pat. No. 5,279,673 filed Jan. 5, 1990; and Ser. No. 461,540 now U.S. Pat. No. 4,997,626 filed Jan. 5, 1990. Each of these applications is incorporated in its entirety by reference herein.

BACKGROUND OF THE INVENTION

This invention relates to disinfecting lenses, such as contact lenses. In particular, the invention relates to methods and compositions useful to quickly and effectively disinfect lenses while reducing eye irritation caused by disinfecting the lenses.

Contact lenses should be periodically disinfected to protect the wearer's eyes from infection and to improve the wearer's comfort. It is often desirable that lens disinfecting be accomplished quickly, e.g., for the convenience of the wearer. However, conventional fast-acting disinfectants that are used with contact lenses have a high potential to cause eye irritation. In fact, the general rule has been that the amount of eye irritation to be expected is directly proportional to the rate of disinfecting. Fast-acting disinfectants, such as hydrogen peroxide, cause significant ocular irritation if placed directly in the eye. Thus, when using such disinfectants a thorough rinsing and/or neutralization step is required to remove substantially all traces of the disinfectant. Thus, in Gaglia, et al U.S. Pat. No. 3,912,451 a metal component is used to remove hydrogen peroxide from soft contact lenses which have been sterilized with hydrogen peroxide. Also, such disinfectants are often not stable and tend to lose their potency over time. A fast-acting, stable lens disinfecting system which is not as prone to cause eye irritation would clearly be advantageous.

It has been proposed to disinfect substrates using an acidic solution containing chlorites, such as sodium chlorite. Alliger U.S. Pat. No. 4,084,747 and International Patent Publication (PCT) No. WO35/04107 are directed to such systems. The acidic conditions apparently cause liberation of chlorine dioxide, which acts as a disinfectant. Lenses, and in particular contact lenses, have not been disclosed as being disinfected in such acidic media. High acidity can cause substantial eye irritation.

Randeri et al U.S. Pat. No. 3,873,696 discloses a system for sterilizing hydrophilic contact lenses with an aqueous, isotonic solution containing an oxygen releasing salt such as potassium peroxymonosulfate or certain chlorine compounds, such as hypochlorites, chlorites, chlorates and perchlorates. Because of the relatively low antimicrobial activity of these sulfur-containing salts or chlorine compounds alone, relatively high concentrations of these materials are needed to provide the desired contact lens treatment in a reasonable period of time. This patent does not disclose the formation of contact lens disinfecting amounts of chlorine dioxide.

In addition to disinfecting the contact lens, it should also be cleaned, e.g., of debris such as protein-based debris which accumulates on the lens during use. Such lens cleaning is often done in the presence of one or more enzymes. See, for example, Karageozian U.S. Pat. No. 3,910,296. In many instances, a complete lens maintenance procedure involves first enzymatic cleaning followed by the separate lens disinfecting step. One system in which lens cleaning and disinfecting occur substantially simultaneously is disclosed in Huth, et al U.S. Pat. No. Re. 32,672. This system employs a solution to contact the lens which comprises a disinfecting amount of peroxide and an effective amount of peroxide-active proteolytic enzyme for a time sufficient to remove substantially all protein accretions and to disinfect the lens.

SUMMARY OF THE INVENTION

New compositions and methods for disinfecting lenses, e.g., contact lenses, have been discovered. These compositions and methods utilize the controlled formation of chlorine dioxide, a very effective contact lens disinfectant. The ability to control the formation of chlorine dioxide allows one to effectively and efficiently ship and store the chlorine dioxide precursor prior to use. Then, substantially on demand, the precursor is activated to provide the desired amount of chlorine dioxide. In addition, the present system preferably provides for maintaining the acidity of the medium in which the lens is present within the physiological range, for example, in the range of about 6 to about 10, so that no acidity adjustment is needed after disinfection. This feature of the present invention substantially reduces the risk of eye irritation caused by the disinfecting procedure.

In one broad aspect, the invention involves methods and compositions for disinfecting a lens, e.g., a contact lens. In one embodiment, a lens to be disinfected is contacted with a composition including a liquid medium and at least one chlorine dioxide precursor. This contacting takes place in the presence of an effective amount of an activator component selected from organic acid anhydride components, oxygen-releasing components and mixtures thereof in an amount to effect formation of chlorine dioxide from the precursor. This contacting results in the lens being disinfected. This contacting preferably occurs so that the pH of the liquid medium is within the physiological range for humans, for example, within the range of about 6 to about 10, more preferably within the range of about 6 to about 8. Maintaining such a pH allows the disinfected lens to be placed directly into the wearer's eye. Alternately, a simple saline rinse or soak of the disinfected lens may be employed before placing the lens back in the wearer's eye.

In another broad aspect of the invention, compositions, which are useful in performing the present methods, are provided and comprise an activator component and a reducing component. The activator component selected is capable of effecting the formation of a lens disinfecting amount of chlorine dioxide from a chlorine dioxide precursor in a liquid medium into which the activator component is released. The reducing component is capable of chemically reducing chlorine dioxide in the liquid medium into which the reducing component is released. The composition is structured so that upon exposure to a liquid medium the reducing component is released after the activator component is released. This sequential release feature of these compositions provides for chlorine dioxide formation to disinfect the lens, and then for the formed or generated chlorine dioxide to be effectively chemically reduced, for example, to reduce eye irritation.

The above-noted compositions may further include at least one solid chlorine dioxide precursor, e.g., sodium chlorite, which is released, e.g., dissolved, in a liquid medium. The activator component effects formation of lens disinfecting amounts of chlorine dioxide from the chlorine dioxide precursor upon release of the activator component into the liquid medium. Alternately, a solid composition, e.g., in the form of an item such as tablet, pill or the like, can be provided which comprises both at least one chlorine dioxide precursor and at least one activator component which are present in amounts effective to produce lens disinfecting amounts of chlorine dioxide in a liquid medium.

In another broad aspect, the lens to be disinfected or the disinfected lens is contacted with at least one enzyme capable of removing debris from a contact lens in an amount effective to remove debris from the lens, preferably the contact lens, being contacted. This removal or cleaning step may be conducted before or after the disinfecting step. In one embodiment, the liquid medium which includes the chlorine dioxide precursor also includes the enzyme. The activator component and/or the reducing component may be present during the enzyme cleaning, for example, in a substantially inactive, e.g., unreleased, form. If the enzyme, chlorine dioxide precursor and activator component are all present during the enzyme cleaning, the activator component should be present in a substantially inactive form. This will allow the cleaning to occur without interference from the presence of chlorine dioxide. For example, the activator component and the reducing component may be present in a delayed release form, e.g., in a tablet, pill, or the like, together with the enzyme which is released first, e.g., substantially immediately on being exposed to the liquid medium. After sufficient time for effective enzymatic cleaning of the lens has elapsed, the active activator component is released. This causes formation of chlorine dioxide and results in disinfecting the enzymatically cleaned lens. After a further period of time, the active reducing component is released to chemically reduce the residual chlorine dioxide present in the liquid medium. Alternately, the enzyme can be present in a delayed release form together with the reducing component. In this embodiment, the enzyme is released after the lens is disinfected. Thus, the enzyme is released at substantially the same time or after the reducing component is released.

The present lens cleaning and disinfecting preferably take place in a single step. The lens wearer does not need to closely monitor the process or to change solutions between the cleaning and disinfecting steps. Preferably, no acidity adjusting is needed because both disinfecting and cleaning occur in the physiological pH range. Overall, the present invention is very easy and effective to use. This encourages the lens wearer to disinfect, and preferably clean, his/her contact lenses frequently, resulting in more comfort and less eye irritation.

DETAILED DESCRIPTION OF THE INVENTION

The present system is applicable for disinfecting all types of lenses, e.g., contact lenses, which are benefited by periodical disinfecting. Such lenses, e.g., conventional hard contact lenses and soft contact lenses, may be made of any suitable material or combination of materials and may have any suitable configuration.

One important feature of the present invention is the use of chlorine dioxide precursors. Such precursors are adapted to provide for controlled formation of disinfecting amounts of chlorine dioxide. Thus, such precursors allow the disinfectant, e.g., chlorine dioxide, to be shipped and stored with minimum loss of disinfecting power. Chlorine dioxide is formed when needed and wanted, i.e., in a liquid medium contacting a lens to be disinfected. As used herein, a disinfecting amount of chlorine dioxide means such amount as will reduce the microbial burden or load by one log order in 3 hours or less, preferably in 1 hour or less, more preferably in 10 minutes or less. Of course, the amount of chlorine dioxide employed should not cause any substantial damage to the lens being treated.

In general, the chlorine dioxide precursors useful in the present invention are those which form or produce chlorine dioxide in a liquid medium, preferably a liquid aqueous medium, in the presence of one or more of the presently useful activator components. The liquid aqueous medium is preferably maintained at a pH in the range of about 6 to about 10, more preferably about 6 to about 8. Among the preferred chlorine dioxide precursors useful in the present invention is stabilized chlorine dioxide. Useful chlorine dioxide precursors include one or more chlorine dioxide-containing complexes and/or one or more chlorite-containing components and/or one or more other entities capable of forming chlorine dioxide in a liquid medium in the presence of the presently useful activator components.

Examples of such chlorite-containing components include metal chlorites, and in particular alkali metal and alkaline earth metal chlorites. A specific example of a chlorite-containing component which is useful as a chlorine dioxide precursor is technical grade sodium chlorite. Among the preferred chlorine dioxide-containing complexes are complexes of chlorine dioxide with carbonate, chlorine dioxide with bicarbonate and mixtures thereof. The exact chemical composition of many of the chlorine dioxide precursors, e.g., stabilized chlorine dioxide, and in particular the chlorine dioxide complexes, is not completely understood. The manufacture or production of certain chlorine dioxide precursors is described in McNicholas U.S. Pat. No. 3,278,447, which is hereby incorporated in its entirety by reference herein. Specific examples of useful chlorine dioxide precursor sources include products such as that sold under the trademark Dura Klor by Rio Linda Chemical Company, Inc. and that sold under the trademark Anthium Dioxide by International Dioxide, Inc. An especially useful chlorine dioxide precursor source is a product sold under the trademark Purogene by Bio-Cide International, Inc. The chlorine dioxide precursor may be included in a liquid medium at a predetermined concentration, e.g., a concentration chosen to provide a disinfecting amount of chlorine dioxide in the presence of the acidic component or components. Preferably, the liquid medium has sufficient chlorine dioxide precursor so as to have a potential of producing chlorine dioxide in the range of about 0.002% to about 3% (weight chlorine dioxide/volume of liquid medium).

In one embodiment, the chlorine dioxide precursor includes a functionality selected from carbonate, borate, sulfate, phosphate, and mixtures thereof.

The presently useful activator components are selected from the group consisting of organic acid anhydride components, oxygen-releasing components and mixtures thereof. Such activator components are capable of effecting the formation of a lens disinfecting amount, preferably a contact lens disinfecting amount, of chlorine dioxide from a chlorine dioxide precursor in a liquid medium into which the activator component is released. The activator component is preferably water soluble. In order to facilitate user convenience and to reduce the risk of eye irritation, the activator component preferably is ophthalmically acceptable. That is, the activator component in the concentrations used in the present invention is preferably such that it has substantially no significant long term detrimental effects on the ocular health of the wearer of a contact lens disinfected in accordance with the present invention.

Organic acid anhydrides effective in accordance with this invention include both open chain and cyclic anhydrides. In the aromatic series, the anhydrides of polybasic acids, such as phthalic acid, are preferred to other anhydrides of this series. Substituted aromatic acid anhydrides may be used, provided readily oxidizable substituents are avoided. Examples of suitable substituent groups include the halogens-fluorine, chlorine, bromine and iodine; alkoxy-such as methoxy, ethoxy, tertiary-butoxy and the like; $NO_2$, and $SO_3H$ and the like. Such groups possess relatively high stability toward oxidation as compared with amino, aldehyde and similar groups which are readily oxidizable.

Aliphatic polybasic carboxylic acids, for example, succinic, glutaric, glutaconic, maleic and the like and mixtures thereof form heterocyclic anhydrides which are suitable for use according to the invention. The anhydrides of the saturated aliphatic polybasic acids, e.g., succinic and glutaric, are preferred to the anhydrides of the unsaturated aliphatic polybasic acids since they are more stable in the presence of oxidizing agents. Substituents of the types mentioned as suitable with respect to aromatic acid anhydrides may be present.

The anhydrides of the saturated monobasic aliphatic acids are suitable for use in the present invention. These are exemplified by the anhydrides of acetic acid, propionic acid, butyric acid, isobutyric acid and the like, and by the anhydrides of the higher molecular weight carboxylic acids, e.g., stearic acid and the like. Preferably, anhydrides of carboxylic acids having 2 to about 30, more preferably 2 to about 20, carbon atoms per molecule are employed. As in the case of the aromatic acid anhydrides and the anhydrides derived from polybasic aliphatic acids, stable substituents may be present. Thus, the anhydrides of chloroacetic, ethoxyacetic, and nitropropionic acids may be used. The anhydrides of substituted or unsubstituted unsaturated open chain monobasic acids may be employed in the present invention provided they are sufficiently stable toward chlorine dioxide and the chlorine dioxide precursor employed.

The amount of anhydride component employed should be such as to be effective to effect formation of a lens disinfecting amount of chlorine dioxide in a chlorine dioxide precursor-containing liquid medium into which the anhydride component is released. The anhydride component is preferably present, for example, during the disinfecting contacting, in an amount in the range of about 0.01 mole or less to about 1 mole or more per mole of potential chlorine dioxide present as chlorine dioxide precursor in the liquid medium. Particularly useful results are achieved using anhydride component in the range of about 0.3 mole to about 1.5 moles per mole of potential chlorine dioxide present as chlorine dioxide precursor in the liquid medium.

Oxygen-releasing components useful in the present invention include both inorganic and organic peroxy compounds.

In one embodiment, the oxygen-releasing components which may be used in the present invention are water soluble inorganic salts such as, for example, the sodium, potassium, calcium, magnesium, lithium and ammonium salts of oxygen-releasing sulfur compounds, such as, for example, the perthiosulfates ($S_2O_5{}^{-2}$), the persulfates ($SO_5{}^{-2}$), the peroxysulfates, such as the peroxymonosulfates ($HSO_5{}^{-1}$) and the peroxydisulfates ($S_2O_8{}^{-2}$), and mixtures thereof.

A particularly preferred oxygen-releasing component is potassium peroxymonosulfate ($KHSO_5$) and the preferred form of this component is the triple salt which is a combination of potassium peroxymonosulfate ($KHSO_5$), potassium hydrogen sulfate ($KHSO_4$) and potassium sulfate ($K_2SO_4$). This composition is an acidic, water soluble, oxygen releasing powder which is odorless, white, granular, stable and free flowing. Other alkali metal, e.g., sodium, and ammonium salts are also useful.

Among useful organic peroxy compounds are the aliphatic and aromatic percarboxylic acids based on the radical

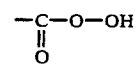

Organic peroxy compounds are preferably the aliphatic or aromatic percarboxylic acids and their alkali metal and ammonium salts. Examples of the aliphatic peracids include peracetic acid, perpropionic acid, up to perlauric acid. The preferred peracids are aromatic such as perbenzoic acid and nuclear substituted perbenzolic acids, especially those having melting points above 50° C. Especially preferred is p-methoxyperbenzoic acid.

The amount of oxygen-releasing component employed should be such as to be effective to effect formation of a lens disinfecting amount of chlorine dioxide in a chlorine dioxide precursor-containing liquid medium into which the oxygen-releasing component is released. The oxygen-releasing component is preferably present, for example, during the disinfecting contacting, in an amount in the range of about 0.01 mole or less to about 1 mole or more per mole of potential chlorine dioxide present as chlorine dioxide precursor in the liquid medium. Particularly useful results are achieved using oxygen releasing component in the range of about 0.01 mole to about 0.1 mole per mole of potential chlorine dioxide present as chlorine dioxide precursor in the liquid medium.

In one embodiment of the present invention, a solid composition is provided which includes at least one chlorine dioxide precursor and at least one activator component. This composition, in the form of a tablet, pill or the like, includes sufficient solid chlorine dioxide precursor and activator component to produce a lens disinfecting amount, preferably a contact lens disinfecting amount, of chlorine dioxide when released in a liquid medium.

The liquid media used are selected to have no substantial detrimental effect on the lens being treated and to allow and even facilitate the present lens treatment or treatments. The liquid media are preferably aqueous-based. A particularly useful liquid aqueous medium is that derived from saline, e.g., a conventional saline solution. During the disinfecting contacting, it is preferred that the liquid aqueous medium have a pH in the range of about 6 to about 10, more preferably about 6 to about 8, and still more preferably about 7.5.

After the disinfecting contacting, the disinfected lens can be contacted with e.g., rinsed and/or soaked in, a second liquid medium, e.g., a conventional saline or buffered saline solution, separate and apart from the liquid medium used in the disinfecting contacting. The second liquid medium preferably has a pH in the range of about 6 to about 10, more preferably about 6 to about 8, and still more preferably about 7.5. Such pH ranges are substantially consistent with the normal physiological pH for humans. Thus, after disinfecting, the disinfected lens may be placed directly in the eye. Alternately, a simple saline rinse or soak of the disinfected lens may be employed before placing the lens in the eye. This is in contrast to other systems which require elaborate neutralization procedures before the lens is suitable for placement in the eye.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. Contacting at or about ambient temperature is very convenient and useful. The contacting preferably occurs at or about atmospheric pressure. This contacting preferably occurs for a time to substantially completely disinfect the lens being treated. Such contacting times can be in the range of about 1 minute to about 12 hours or more.

In one embodiment, a composition is provided which includes at least one enzyme and at least one activator component, as described elsewhere herein. The composition is structured so that upon introduction into a liquid medium, the enzyme is released before the activator component is released.

The enzyme/lens contacting occurs in a liquid medium, preferably an aqueous liquid medium, such as described elsewhere herein. In a particularly useful embodiment, the enzyme/lens contacting occurs in the same container as does the lens disinfecting, more particularly in the same liquid medium as does the lens disinfecting. This "one-step" disinfecting/cleaning system is effective and very convenient for the lens wearer to use.

Among the types of debris that form on contact lens during normal use are protein-based or proteinaceous debris, mucin-based debris, lipid-based debris and carbohydrate-based debris. One or more types of debris may be present on a single contact lens.

The enzyme or enzymes used are capable of removing at least one type of debris from a contact lens. The amount of such enzyme or enzymes used is preferably effective to remove substantially all of at least one type of debris from a debris laden contact lens in a reasonable time, preferably within about 12 hours, for example, in the range of about 1 minute to about 12 hours, and more preferably within about 2 hours, for example, about 1 minute to about 2 hours. The active enzyme-containing liquid medium preferably contains sufficient enzyme to provide between about 0.0001 to about 5 Anson units of activity, more preferably between about 0.001 or about 0.01 to about 0.1 or about 1 Anson unit, per single lens treatment. Higher or lower amounts may be used.

The enzyme employed may be selected from enzymes which are conventionally employed in the enzymatic cleaning of contact lenses. For example, many of the enzymes disclosed in Huth et al U.S. Pat. No. Re. 32,672 and Karageozian et al U.S. Pat. No. 3,910,296 are useful in the present invention. Each of these patents is incorporated in its entirety by reference herein. Among the useful enzymes are those selected from proteolytic enzymes, lipases and mixtures thereof. The enzyme may be one or more carbohydrate-active or carbolytic enzymes. Specific examples of useful enzymes include proteases, amylases, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases from Bacillus Species" Biochemical and Biophysical Research Comm., Vol 34, No. 5, pp 600–604, (1969).

The subtilisin enzymes are broken down into two sub-classes, subtilisin A and subtilisin B. In the subtilisin A grouping are enzymes derived from such species are *B. subtiis, B. licheniformis and B. pumilis.* Organisms in this sub-class produce little or no neutral protease or amylase. The subtilisin B sub-class is made up of enzymes from such organisms a *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens deposited due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective lens cleaner will depend on several factors, including the inherent activity of the enzyme.

Enzyme activity is pH dependent so for any given enzyme, there is a particular pH range in which that enzyme will function best. The determination of such range can readily be done by known techniques.

It has been found that many of the effective lens cleaning enzymes, such as described elsewhere herein, are inactivated in the presence of certain contact lens disinfectants. For example, a substantial number of such enzymes are inactive in the presence of disinfecting amounts of chlorine dioxide. Since the use of such enzyme incompatible (or simply incompatible) contact lens disinfectants is often advantageous in the contact lens disinfecting context, a system to allow both such disinfecting and enzymatic cleaning of contact lenses, preferably in one user initiated step, would clearly be advantageous. The present invention provides such a system.

The present compositions may comprise an effective debris removing amount of at least one enzyme capable of removing debris from a contact lens and at least one reducing component capable of chemically reducing chlorine dioxide. The reducing component may also act to inactivate or destroy the residual activator component, for example, the oxygen-releasing component. In any event, the composition is structured, such as in a delayed release configuration, so that the enzyme is released in a liquid medium containing the chlorine dioxide at substantially the same time or after the reducing component is released in the liquid medium. Using this composition, the enzyme is allowed to remove debris from the contact lens in the liquid medium, with no substantial interference from the chlorine dioxide, which is often incompatible with the active enzyme.

Any suitable reducing component may be used in the present invention, provided that it functions as described herein and has no substantial detrimental effect on the lens being treated and on the human wearing the treated lens. The reducing component is preferably included to chemically reduce substantially all the chlorine dioxide remaining in the liquid medium, particularly after the lens is disinfected.

Examples of useful reducing components include, but are not limited to, SH (group) - containing water soluble lower alcohols, N-acetylcysteine, acetylcysteine, cysteine hydrochloride ethyl ester, glutathione, homocysteine, carbamoylcysteine, cysteine, cysteine hydrochloride, dithiothreitol, sodium bisulfite, thio urea, beta-mercaptoethanol, cysteinyl glycine, 2-mercaptopropionic acid, 2-mercaptopropionylglycine, 2-mercaptoethylamine hydrochloride, dithioerythritol, sodium metabisulfite, sulfites, pyrosulfites, dithionites and the like. A particularly useful example of such a reducing component is N-acetylcysteine. The amount of the reducing component used is such to chemically reduce the desired amount of chlorine dioxide, and, if necessary, the oxygen-releasing component. In one embodiment, the amount of reducing component employed is about 50% to about 150% that amount needed to chemically reduce all the chlorine dioxide and oxygen-releasing component present in the liquid medium when the reducing component is released in the liquid medium. The amount of reducing component used is preferably at least that amount needed to chemically reduce all the chlorine dioxide present in the liquid medium when the reducing component is released in the liquid medium.

In another embodiment, the activator component is included in the composition in a substantially inactive form and/or is released on a delayed release basis. For example, the enzyme, activator component and reducing component may be present together in a single item, i.e., a layered tablet, pill or the like. After the item is introduced with the liquid medium containing the chlorine dioxide precursor, the enzyme first becomes available to remove debris from the to-be-cleaned lens. At this time, i.e., when the enzyme is cleaning the lens, the activator component and the reducing component remain in the item, effectively out of contact with the chlorine dioxide precursor. After a period of time, e.g., a predetermined period of time for which the item is designed, the activator component is released into the liquid medium. This causes chlorine dioxide formation which, in turn, results in disinfecting the lens in the liquid medium. After a second period of time, the reducing component is released into the liquid medium containing the disinfected lens to chemically reduce the residual chlorine dioxide and oxygen-releasing component present in this liquid medium, as described elsewhere herein.

Tablets, pills or the like which release their ingredients in a sequential, time delayed manner are well known and can be produced using conventional technology. Therefore, a detailed description of such items and such production technology is not presented here. However, such tablets, pills or the like are preferably designed to allow one component sufficient time to perform its function before releasing another component which may interfere with the functioning of the first component. For example, if the item contains both an enzyme and an activator component, the item is preferably designed to allow the enzyme sufficient time to remove at least a major amount, and more preferably substantially all, of at least one type of debris, for example, protein-based debris, from the lens in the liquid medium. In other words, such items are preferably designed so that sufficient time elapses between release of the enzyme and release of the activator component to allow the enzyme to perform its cleaning function. Such sufficient time is preferably in the range of about one minute to about 2 hours, more preferably about five minutes to about one hour.

Whether or not the enzyme is present in the composition (delayed release item), the composition is preferably designed to allow the activator component to be released before the reducing component. The interval between the time the activator component is released and the time the reducing component is released is preferably sufficient to provide for the chlorine dioxide which is formed after release of the activator component to disinfect the lens. This interval is preferably in the range of about 1 minute to about 12 hours, more preferably about 0.2 to about 4 hours.

Although multi-layered (including core and coating layering) tablets or pills are preferred, the delayed release form of the present compositions can be present in any other suitable item or items, such as masses of powders, granules and the like. Delayed release technology is well known in the art as exemplified by the text *Controlled Drug Delivery*, 2nd Ed., Joseph R. Robinson & Vincent H. L. Lee, Eds., Marcel Dekker, Inc., New York, 1987.

Any suitable delayed release component or combination of delayed release components may be employed, provided that such component or components function as described herein and have no substantial detrimental effect on the other components present, on the lens being treated and on the human wearing the treated lens. The delayed release component is preferably at least partially, more preferably completely, water soluble. The delayed release component preferably comprises a major amount of at least one polymeric material. Examples of useful delayed release components include, but are not limited to, soluble cellulose ethers such as methylcellulose, methylhydroxypropylcellulose, methylhydroxyethylcellulose, hydroxypropylcellulose, hydroxyethylcellulose and sodium carboxymethylcelluloses; cellulose esters such as cellulose acetate phthalate and hydroxypropylmethylcellulose phthalate; polymers derived from at least one of acrylic acid, acrylic acid esters, methacrylic acid and methacrylic acid esters such as methacrylic acid-methyl methacrylate copolymer (for example that sold by Rohm Pharma under the trademark Eudragit L 100) and methacrylic acid-ethyl acrylate copolymers (for example that sold by Rohm Pharma under the trademark Eudragit L 30D); polymers derived from methyl vinyl ether and maleic acid anhydride; polyvinylpyrrolidone; polyvinyl alcohols and the like and mixtures thereof.

The following examples illustrate certain aspects of the present invention.

EXAMPLES 1 TO 8

A series of eight (8) activator tablets were prepared. These tablets had compositions as shown in Table 1.

TABLE 1

Chlorine Dioxide Activator Tablet Formulations

| Ingredients | Milligrams per tablet | | | |
|---|---|---|---|---|
| Oxone(1) | 1.5 | 0.5 | 0.25 | 0.05 |
| Succinic anhydride | — | — | — | — |
| Polyvinyl-pyrollidone | 0.3 | — | — | — |
| Subtilisin A | 0.5 | — | — | — |
| Sugar-based binder/filler | 35.0 | 35.0 | 35.0 | 35.0 |
| Sodium carbonate, anhydrous | 18.0 | 18.0 | 18.0 | 18.0 |
| Tartaric acid | 7.0 | 7.0 | 7.0 | 7.0 |
| Polyethylene glycol 3350(2) | 6.0 | 6.0 | 6.0 | 6.0 |
| Tablet weight(mg) | 68.3 | 66.5 | 66.25 | 66.05 |
| Formula No. | I | II | III | IV |
| Oxone(1) | — | — | — | — |
| Succinic anhydride | 10.0 | 1.25 | 0.75 | 0.25 |
| Sodium chlorite | 0.2 | — | — | — |
| Polyvinyl-pyrrolidone | 0.3 | — | — | — |
| Subtilisin A | 0.5 | — | — | — |
| Sugar-based binder/filler | 35.0 | 30.0 | 30.0 | 30.0 |
| Sodium carbonate, anhydrous | 28.0 | 19.0 | 19.0 | 17.0 |
| Tartaric acid | 5.0 | 7.0 | 7.0 | 7.0 |
| Polyethylene glycol 3350(2) | 6.0 | 4.0 | 4.0 | 4.0 |
| Tablet weight(mg) | 85.0 | 61.25 | 60.75 | 58.25 |
| Formula No. | V | VI | VII | VIII |

(1) Tradename for a triple salt combination of $KHSO_4$, $K_2SO_4$ and $2KHSO_5$.
(2) A conventional tabletting aid having a molecular weight of about 3350.

Each of these activator tablets was tested for chlorine dioxide generation using a standard solution. This solution was purified water with the following components: 0.85% (w/v) sodium chloride; 0.10% (w/v) boric acid; and 0.005% (w/v) a stabilized chlorine dioxide product sold by Bio-Cide International, Inc. under the trademark Purogene ®. The pH of this solution was buffered to about 7.7.

Each of the activator tablets was placed in 10 ml of the solution and the resulting material was monitored for chlorine dioxide concentration.

Results of these tests are shown in Table 2.

TABLE 2

Chlorine Dioxide Generation from Activator Tablets

| Time (min) | | $ClO_2$ Concentration, ppm by wt. | | | |
|---|---|---|---|---|---|
| | | 0.05 | 0.25 | 0.5 | 1.5 |
| 0 | Oxone(mg/tab)*: | 0 | 0 | 0 | 0 |
| 80 | | 0.6 | 2.3 | 4.8 | 0.4 |
| 120 | | 0.9 | 3.3 | 5.6 | — |
| 190 | | 1.4 | 4.0 | 6.1 | — |
| 320 | | 1.8 | 3.7 | 5.1 | — |
| 400 | | 1.9 | 3.6 | 4.3 | — |

| Time (min) | | $ClO2$ Concentration, ppm by wt. | | | |
|---|---|---|---|---|---|
| | | 0.25 | 0.75 | 1.25 | 10.0 |
| 0 | Succinic Anhydride(mg/tab) | 0 | 0 | 0 | 0 |
| 15 | | 0.3 | 1.2 | 1.7 | — |
| 30 | | 0.3 | 0.8 | 1.7 | — |
| 45 | | 0.3 | 0.7 | 1.3 | — |
| 60 | | 0.3 | 0.7 | 1.9 | — |
| 90 | | 0.2 | 0.9 | 1.9 | 0.8 |

Each of the activator tablets tested effected the generation of sufficient chlorine dioxide to disinfect a contact lens within a reasonable period of time.

EXAMPLES 9 TO 16

An activator tablet having the composition of each of the activator tablets identified in Examples 1 to 8 was tested as follows. The activator tablet was placed in 10 ml of a solution of 0.005% (w/v) the stablilized chlorine dioxide product noted in Examples 1 to 8 in purified water. After the tablet had dissolved, the pH and osmolality of the solution was determined.

Results of these tests are shown in Table 3.

TABLE 3

Physical Properties of Activator Tablets Dissolved in 50 ppm Stabilized Chlorine Dioxide Solution

| Solution | | pH | Osmolality(mOsm/kg) |
|---|---|---|---|
| Succinic anhydride: | 0.25 mg/10 ml | 7.8 | 310 |
| | 0.75 mg/10 ml | 8.0 | 320 |
| | 1.25 mg/10 ml | 7.8 | 311 |
| | 10.00 mg/10 ml | 7.5 | 369 |
| Oxone: | 0.05 mg/10 ml | 7.8 | 340 |
| | 0.25 mg/10 ml | 7.8 | 341 |
| | 0.50 mg/10 ml | 7.8 | 341 |
| | 1.50 mg/10 ml | 7.9 | 348 |

These results indicate that the present activator tablets provide contact lens disinfecting media which have ophthalmically acceptable pHs and osmolalities. This is a substantial advantage of the present invention since no additional neutralization or acidity adjusting step is required. The disinfected lens can be removed from this solution and placed directly in the eye with little or no risk of eye irritation or discomfort.

EXAMPLE 17

A lens disinfecting system is provided which included a solution, an activator tablet and a neutralizer tablet.

The solution is purified water with the following components: 0.85% (w/v) sodium chloride; 0.10% (w/v) boric acid; and 0.005% (w/v) the stabilized chlorine dioxide product identified in Examples 1 to 8. The pH of this solution is about 7.7.

The activator tablet is as shown above as Formula No. II. The neutralizer tablet has the following composition: 23.3 mg sugar-based binder/filler; 1.5 mg. polyethylene glycol (molecular weight of about 3350); and 1.2 mg N-acetylcysteine.

The activator tablet is placed in 10 ml of the solution along with a contact lens to be disinfected.

After one hour, the neutralizer tablet is then placed in the material. The neutralizer tablet dissolves in the material. Upon shaking the material, the characteristic color of chlorine dioxide which was present disappears immediately.

The amount of chlorine dioxide produced by combining the activator tablet with the solution is effective to kill most microorganisms in about 30 minutes or less.

The neutralizer tablet is added to the solution to consume chlorine dioxide. The disinfected contact lens can be taken from the system and placed directly in the eye without irritation or discomfort.

EXAMPLE 18

Example 17 is repeated except that the activator tablet employed has the composition of Formula No. VI.

Substantially similar results to those obtained in Example 17 are achieved here.

EXAMPLE 19

A lens disinfecting system is provided which is the same as tat in Example 17 except for the composition of the neutralizer tablet.

In the present system, the neutralizer tablet has the following composition: 4.5 mg N-acetylcysteine; 2.4 mg polyethylene glycol (molecular weight of about 3350) 6.39 mg sugar-based binder/filler; and 0.71 mg Subtilisin A.

This system functions in much the same manner as the system of Example 17 except that the Subtilisin A is released with the other components of the neutralizer tablet. Thus, enzymatic cleaning of the lens in the solution begins. The enzymes can be inactivated by chlorine dioxide. However, the chlorine dioxide is removed from the solution sufficiently rapidly so that the enzyme remains effective to clean the lens. The disinfected and cleaned lens is then removed from the system, rinsed with a conventional saline solution to remove residual enzyme and placed in the eye without irritation or discomfort.

EXAMPLE 20

Example 19 is repeated except that the activator tablet used in Example 18 is employed.

Substantially similar results to those obtained in Example 19 are achieved here.

EXAMPLE 21

Using conventional techniques, a layered delayed release tablet is prepared. The core of this tablet has the same chemical make-up as the neutralizer tablet of Example 17. The outer layer of this tablet has the same chemical make-up as Formula No. II. A delayed release barrier layer is located between the core and the outer layer and is designed to delay the release of the neutralizer core in the solution for one hour after the layered tablet is introduced into the solution.

The solution which is used is as identified in Example 17.

The contact lens to be disinfected and the layered tablet are initially introduced into 10 ml of the solution at substantially the same time. The outer layer of the tablet dissolves into the solution very quickly and effects the generation of a contact lens disinfecting amount of chlorine dioxide. After one hour, the neutralizer core is released to consume chlorine dioxide. The disinfected lens is then taken from the system and placed directly in the eye without irritation or discomfort.

EXAMPLE 22

Example 21 is repeated except that the core of the layered tablet has the same chemical make-up as the neutralizer tablet of Example 19.

The contact lens is disinfected substantially as set forth in Example 21. In addition, the Subtilisin A enzyme in the neutralizer core is effective to clean the lens of proteinaceous debris.

The disinfected and cleaned lens is then taken from the system, rinsed with a conventional saline solution to remove residual enzyme and placed in the eye without irritation or discomfort.

While this invention has been described with respect to various specific examples and embodiments, it is to be understood that the invention is not limited thereto and that it can be variously practiced within the scope of the following claims.

What is claimed is:

1. A method for disinfecting a lens which comprises: contacting a lens in a liquid medium with a chlorine dioxide precursor in the presence of an effective amount of an activator component selected from the group consisting of organic acid anhydride components, oxygen-releasing components and mixtures thereof to effect formation of a lens disinfecting amount of chlorine dioxide from said chlorine dioxide precursor in said liquid medium, thereby disinfecting said lens, said organic acid anhydride components being selected from the group consisting of anhydrides of carboxylic acids having 2 to about 30 carbon atoms and mixtures thereof, and said oxygen-releasing components being selected from the group consisting of perthiosulfates, persulfates, peroxysulfates and mixtures thereof.

2. The method of claim 1 wherein said liquid medium is an aqueous liquid medium and said contacting occurs at a pH in the range of about 6 to about 10, and said lens is a contact lens.

3. The method of claim 1 wherein said activator component comprises an organic acid anhydride selected from the group consisting of succinic anhydride, glutaric anhydride, glutaconic anhydride, maleic anhydride and mixtures thereof.

4. The method of claim 1 wherein both said chlorine dioxide precursor and said activator component are initially solid and are introduced into said liquid medium at substantially the same time.

5. The method of claim 1 which further comprises introducing a reducing component effective to chemically reduce at least a portion of the chlorine dioxide formed from said chlorine dioxide precursor in said liquid medium.

6. The method of claim 1 which further comprises contacting the lens in a liquid medium with at least one enzyme in an amount effective to remove debris from the lens.

7. The method of claim 6 wherein said enzyme and said activator component are each part of a single item introduced into said liquid medium.

8. The method of claim 7 wherein said item further comprises a delayed release component in an amount effective to release said enzyme prior to releasing said activator component.

9. A composition comprising a liquid medium including a chlorine dioxide precursor in an amount effective to form a lens disinfecting amount of chlorine dioxide; an activator component selected from the group consisting of organic acid anhydride components, oxygen-releasing components and mixtures thereof, said organic acid anhydride components being selected from the group consisting of anhydrides of carboxylic acids having 2 to about 30 carbon atoms and mixtures thereof, and said oxygen-releasing components being selected from the group consisting of perthiosulfates, persulfates, peroxysulfates and mixtures thereof, said activator component being present in an amount effective to effect the formation of a lens disinfecting amount of chlorine dioxide from said chlorine dioxide precursor; and a reducing component in an amount effective to chemically reduce all the chlorine dioxide in said liquid medium.

10. The composition of claim 9 wherein said activator component comprises an organic acid anhydride selected from the group consisting of succinic anhydride, glutaric anhydride, glutaconic anhydride maleic anhydride, and mixtures thereof.

11. The composition of claim 9 wherein said activator component and said reducing component are present in a combination which further comprises at least one enzyme in an amount effective to substantially remove at least one type of debris from a debris laden contact lens and a delayed release component in an amount effective so that upon introduction into said liquid medium said enzyme is released before or after said activator component is released.

12. The composition of claim 9 wherein said activator component and said reducing component are present in a combination which further comprises a delayed release component in an amount effective so that upon introduction into said liquid medium said reducing component is released from said combination after said activator component is released from said combination.

13. A composition comprising at least one enzyme effective to remove debris from a contact lens; an activator component selected from the group consisting of organic acid anhydride components, oxygen-releasing components and mixtures thereof, said organic acid anhydride components being selected from the group consisting of anhydrides of carboxylic acids having 2 to about 30 carbon atoms and mixtures thereof, and said oxygen-releasing components being selected from the group consisting of perthiosulfates, persulfates, peroxysulfates and mixtures thereof, said activator component being present in an amount effective to effect the formation of a lens disinfecting amount of chlorine dioxide from a chlorine dioxide precursor in a liquid medium; and a delayed release component in an amount effective so that upon introduction of said composition into a liquid medium said enzyme is released into the liquid medium before said activator component is released into the liquid medium.

14. The composition of claim 13 which further comprises a chlorine dioxide precursor capable of forming chlorine dioxide in a liquid medium in the presence of said activator component.

15. A composition comprising a solid chlorine dioxide precursor capable of forming chlorine dioxide in a liquid medium; and a solid activator component selected from the group consisting of organic acid anhydride components, oxygen-releasing components and mixtures thereof, said organic acid anhydride components being selected from the group consisting of anhydrides of carboxylic acids having 2 to about 30 carbon atoms and mixtures thereof, and said oxygen-releasing components being selected from the group consisting of perthiosulfates, peroxysulfates and mixtures thereof, said solid activator component being present in an amount effective to effect formation of a lens disinfecting amount of chlorine dioxide from a chlorine dioxide precursor in a liquid medium.

* * * * *